United States Patent
McNeirney

(10) Patent No.: US 7,246,621 B2
(45) Date of Patent: Jul. 24, 2007

(54) REMOVAL OF CARBON DIOXIDE AND CARBON MONOXIDE FROM PATIENT EXPIRED GAS DURING ANESTHESIA

(75) Inventor: John C. McNeirney, Fairburn, GA (US)

(73) Assignee: Minrad Inc., Buffalo, NY (US)

( * ) Notice: Subject to any disclaimer, the term of this patent is extended or adjusted under 35 U.S.C. 154(b) by 0 days.

(21) Appl. No.: 11/098,243

(22) Filed: Apr. 4, 2005

(65) Prior Publication Data

US 2005/0257790 A1 Nov. 24, 2005

Related U.S. Application Data

(60) Provisional application No. 60/559,659, filed on Apr. 5, 2004.

(51) Int. Cl.
*A62B 7/10* (2006.01)
(52) U.S. Cl. .................... 128/205.12; 128/203.12; 55/26; 95/11
(58) Field of Classification Search ........... 128/203.28, 128/204.28, 205.13, 205.12, 205.16, 205.24, 128/205.28, 205.29; 600/532, 538; 95/11; 55/26

See application file for complete search history.

(56) References Cited

U.S. PATENT DOCUMENTS 3,140,931 A * 7/1964 McRobbie
4,222,750 A * 9/1980 Gauthier et al. ............ 95/102
4,534,346 A * 8/1985 Schlaechter ............ 128/205.12
4,799,374 A * 1/1989 Bossart et al. .............. 77/1 G
4,810,265 A * 3/1989 Lagree et al. ................ 95/101
5,515,845 A * 5/1996 Filipovic et al. ....... 128/205.12
5,520,169 A * 5/1996 Georgieff et al. ...... 128/204.16
5,917,135 A * 6/1999 Michaels et al. ............ 95/11
7,066,985 B2 * 6/2006 Deane et al. .................. 95/96
2005/0072425 A1 * 4/2005 Spearman et al. ..... 128/204.17

* cited by examiner

Primary Examiner—Justine R. Yu
Assistant Examiner—Shumaya Ali
(74) Attorney, Agent, or Firm—Hodgson Russ LLP

(57) ABSTRACT

A method and system for the application of molecular sieves to the removal of carbon dioxide and carbon monoxide from the patient expired gases during anesthesia. The system is especially useful in anesthesia using any of the halogenated ether inhalation anesthetic agents. The expired gases are dried using a non-reactive desiccant to remove water, passed through a filter capable of removing particles larger than 0.3 microns, passed through a bed containing either natural or synthetic molecular sieves capable of removing carbon dioxide and carbon monoxide and then returned to the breathing circuit for recirculation to the patient.

24 Claims, 2 Drawing Sheets

REMOVAL OF CARBON DIOXIDE AND CARBON MONOXIDE FROM PATIENT EXPIRED GAS DURING ANESTHESIA

CROSS REFERENCE TO A RELATED APPLICATION

Applicant claims priority based on U.S. provisional application No. 60/559,659 filed Apr. 5, 2004 and entitled "Removal of Carbon Dioxide and Carbon Monoxide From Patient Expired Gas During Anesthesia," which is incorporated herein by reference.

BACKGROUND OF THE INVENTION

Halogenated ethers such as sevoflurane, isoflurane, enflurane, desflurane and halothane are used as inhalation anesthetic agents worldwide. Typically these agents are used in closed or semi-closed anesthesia circuits wherein all, or some portion of, the patient expired gases containing the agent are rebreathed. In these anesthesia circuits, the carbon dioxide ($CO_2$) expired by the patient must be removed to prevent its buildup that would cause hypoxia in the patient. The present universal practice for removal of $CO_2$ in these systems is to pass the expired gases through a bed of alkali bases which convert the $CO_2$ first to carbonic acid then bind it as an alkali carbonate. However, all of the halogenated ethers suffer some level of degradation in the presence of strong bases which results in the formation of undesirable by-products among which are carbon monoxide, formats and, in the case of sevoflurane, two olefinic compounds, pentafluoroisopropenyl fluoromethyl ether, (PIFE, C4H2F6O), also known as Compound A, and pentafluoromethoxy isopropyl fluoromethyl ether, (PMFE, C5H6F6O), also known as Compound B. Compound A has been shown to be nephrotoxic in rats. Further it is known that the basic materials presently in use are inefficient at the removal of carbon monoxide, some of which is endogenous due to the natural breakdown of various hemoglobin compounds in the mammalian circulatory system.

SUMMARY OF THE INVENTION

The invention uses molecular sieves to remove the $CO_2$ and CO by mechanically preferentially sequestering these compounds within the micro-pore structure of the sieve while not causing degradation of the halogenated ethers. The sieves can be regenerated in-situ using well known techniques such as pressure swing desorption, vacuum swing desorption, a combination of both or temperature swing desorption. An additional feature of the invention is the provision of a heated air purge capability by which the sieve beds can be pasteurized to remove any pathogenic microorganisms that may have penetrated the micro-filter.

The halogenated ether anesthetic agents are used, either alone or in combination with other drugs, in an estimated 80% of the general anesthesia surgical procedures globally.

The benefits of the invention are;

Increased patient safety—by eliminating the degradation products of the halogenated ethers the patient outcomes especially in long or frequent exposure are improved. Also the removal of endogenous carbon monoxide from the anesthetic circuit increases patient safety.

Economics—this is especially true with sevoflurane. The risk of toxicity from compound A is sufficiently high that, in the US, it must be used in high flow rate anesthesia where the gas flow rates are in the 5-6 liter per minute range since this reduces the contact time of the ether in the presence of the alkali base absorber. Sevoflurane cost is around $200 per 250 ml as compared to isoflurane at $35 per 250 ml. Since low flow anesthesia, i.e. flow rates about 1 liter per minute, is desirable in pediatric cases and in some adults, there is the opportunity to reduce the amount of sevoflurane anesthetic agent used in a case by about 70%.

The foregoing additional advantages and characterizing features of the invention will be clearly apparent upon a reading of the ensuing detailed description together with the included drawing.

DETAILED DESCRIPTION OF THE INVENTION

The invention is a method and a system for the application of molecular sieves to the removal of carbon dioxide and carbon monoxide from the patient expired gases during anesthesia. The system and method are especially useful in anesthesia using any of the halogenated ether inhalation anesthetic agents. The expired gases are dried using a non-reactive desiccant to remove water, passed through a filter capable of removing particles larger than 0.3 microns, passed through a bed containing either natural or synthetic molecular sieves capable of removing carbon dioxide and carbon monoxide and then returned to the breathing circuit for recirculation to the patient.

Figure 1:
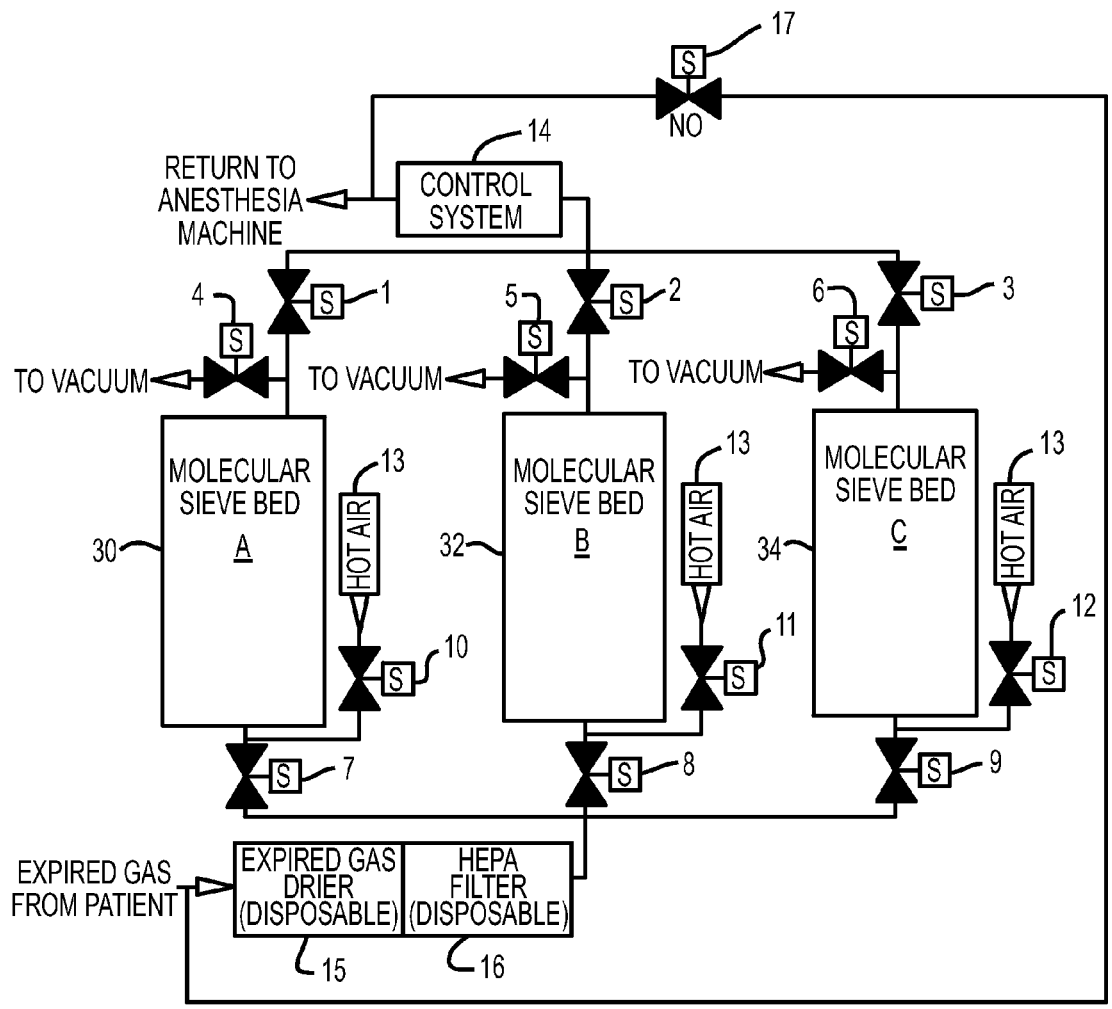
FIG. 1 is a schematic diagram illustrating the system and method of the invention.

Key To FIG. 1

The system of the invention is shown in FIG. 1 and has the following components:

A, B, C Suitable containers containing molecular sieves also designated 30, 32 and 34 of a type selective for Carbon Dioxide and Carbon Monoxide removal from mixed gas streams. Sieve Types A3, A4, X13 for example. Examples of sieve pellet materials are Zeolite and carbon fiber. The preferred form of the sieves is as pellets having a diameter such that it minimizes gas flow resistance through the sieve bed. However, honeycomb structures of sieves may also be used. Although three sieve beds are shown in the illustrative arrangement of FIG. 1, additional beds can be employed if desired. The minimum number of beds is two if in-situ regeneration is desired, i.e. one bed is regenerated while the other is operating on the expired gas from the patient.

1, 2, 3 These are normally closed solenoid valves used to either allow or stop the outflow of gases from the molecular sieve beds to the anesthesia machine.

4, 5, 6 These are normally closed solenoid valves used to either allow or stop the outflow of gases from the molecular sieve beds to a local source of vacuum.

7, 8, 9 These are normally closed solenoid valves used to either allow or stop the inflow of expired gases from the patient to the molecular sieve beds.

10, 11, 12 These are normally closed solenoid valves used to either allow or stop the flow of hot air into the molecular sieve beds.

Figure 2:
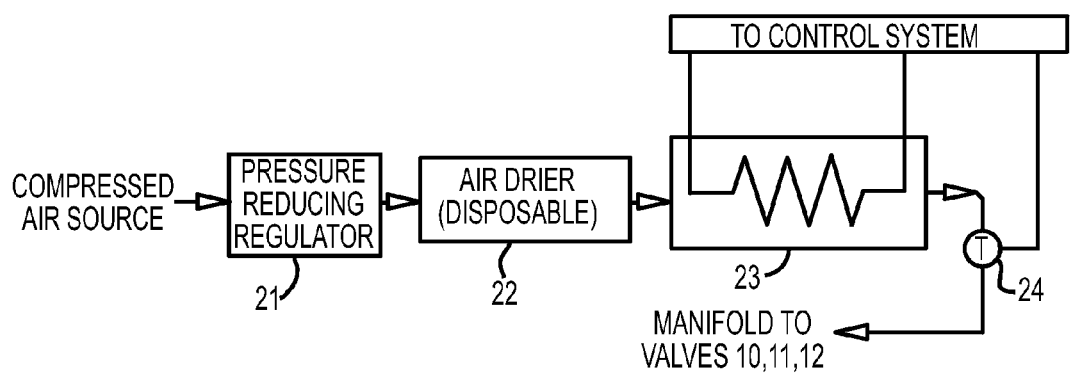
FIG. 2 is a schematic diagram of a hot air source for the heated air purge aspect of the system of FIG. 1.

13 Pressurized hot air source (see FIG. 2)

Figure 3:
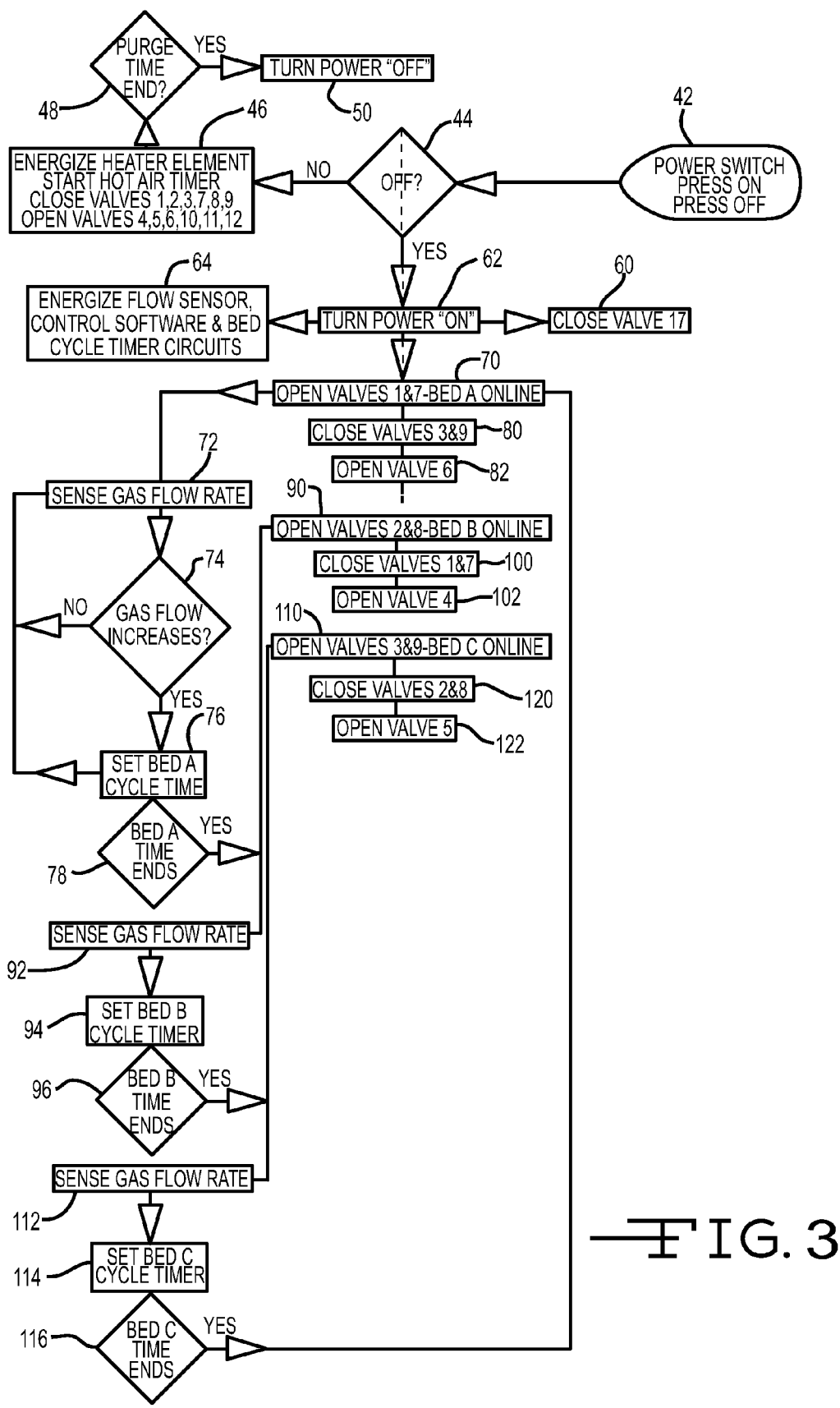
FIG. 3 is a flow diagram illustrating operation of the system and method of the invention.

14 Control System to monitor and control the action sequences of the system (see FIG. 3). Control system 14 controls, among other things, the opening and closing of valves 1-12.

15 An in-line element containing a desiccant which removes water vapor from the expired gas stream such as silica gel which may contain an indicator of activity.

16 HEPA filter—a high efficiency micro filter which removes particles (including micro-organisms) from the dried expired gas stream.

17 This is a normally open solenoid valve that bypasses the system in the event of power failure or a system flow obstruction.

Key To FIG. 2

The pressurized hot air source 13 of the system of FIG. 1 has the following components:

21 This is a standard two-stage regulator to reduce the typical compressed air line pressure available in the operating room (90 psig) to a low pressure consistent with pressure rating of the adsorber system.

22 An in-line element containing a desiccant which removes water vapor from the expired gas stream such as silica gel which may contain an indicator of activity.

23 This is an in-line heating unit containing an resistive electric element which is connected to, and controlled by, the CONTROL SYSTEM (see FIG. 1 14).

24 This is a temperature sensor connected to the CONTROL SYSTEM (see FIG. 1 14) and provides process input to the CONTROL SYSTEM to enable control of the heating unit.

The sieves useful in this application are classed as A3, A4, A5, A7 and X13. The numbers refer to the pore diameters in angstroms. The filter shown in FIG. 1 is known as a HEPA filter. HEPA stands for High Efficiency Particulate Arrestance and is a standard term. A true HEPA filter will remove 99.97% of all particles larger than 0.3 micron which is smaller than the bacteria, spores, molds, yeasts etc.

The operation of the system of FIGS. 1 and 2 is illustrated by the flow diagram of FIG. 3. The operations designated 42, 44, 46, 48 and 50 are associated with the hot air purge feature provided by components 10, 11, 12 and 13 of FIG. 1 and the components of FIG. 2. As indicated by the operation designated 44, the heated air purge operation does not occur when the sieve beds 30, 32 and 34 are operating in the anesthesia circuit.

The operations designated 60, 62 and 64 in FIG. 3 function to place the system of FIG. 1 in operation in the anesthesia circuit. The anesthesia circuit includes the patient, the system of FIG. 1 and the anesthesia machine. The operations designated 70, 72, 74, 76 and 78 are associated with bed A (also designated 30) operating to remove $CO_2$ and CO from patient expelled gas returning the treated or processed gas to the anesthesia machine. Operation 70 opens the inlet and outlet valves 7 and 1, respectively, to connect bed A in the anesthesia circuit. Valve 4 is closed. Operation 74 insures that Bed A is set in timed operation only when an increase in the flow of patient expired gas is sensed. During operation of bed A, operations 80 and 82 cause in-situ regeneration of bed C (also designated 34) by closing the inlet and outlet valves 9 and 3, respectively, and opening valve 6 to place the bed C in communication with a source of vacuum to effect vacuum swing desorption in a known manner.

Bed A is operated for a time determined by operation 76 whereupon at the end of the operating cycle as sensed and indicated by operation 78, bed B (also designated 32) is placed in operation. In particular, the operations designated 90, 92, 94 and 96 are associated with bed B operating to remove $CO_2$ and CO from patient expelled gas and returning the treated or processed gas to the anesthesia machine. Operation 90 opens the inlet and outlet valves 8 and 2, respectively, to connect bed B in the anesthesia circuit. Valve 5 is closed. During operation of bed B, operations 100 and 102 cause in-situ regeneration of bed A by closing the inlet and outlet valves 7 and 1, respectively, and opening valve 4 to place the bed A in communication with a source of vacuum to effect vacuum swing desorption in a known manner.

Bed B is operated for a time determined by operation 94 whereupon at the end of the operating cycle as sensed and indicated by operation 96, bed C (also designated 34) is placed in operation. In particular, the operations designated 110, 112, 114 and 116 are associated with bed C operating to remove $CO_2$ and CO from patient expelled gas and returning the treated or processed gas to the anesthesia machine. Operation 110 opens the inlet and outlet valves 9 and 3, respectively, to connect bed C in the anesthesia circuit. Valve 6 is closed. During operation of bed C, operations 120 and 122 cause in-situ regeneration of bed B by closing the inlet and outlet valves 8 and 2, respectively, and opening valve 5 to place the bed B in communication with a source of vacuum to effect vacuum swing desportion in a known manner.

Bed C is operated for a time determined by operation 114 whereupon at the end of the operating cycle as sensed and indicated by operation 116, bed A is placed in operation. The sequence of operations previously described is continued, and the sequence is repeated for the duration of operation of the anesthesia machine. The time durations of operation of the beds A, B and C as set by operations 76, 94 and 114, respectively, are determined according to the length of time each bed can be operated prior to requiring regeneration in a manner well-known to those skilled in the art.

Literature references related to the degradation of the anesthetic agents:

1. Mono M. Fuji; K. Mukai S, Kodama G. Decomposition of halothane by soda lime and the metabolites of halothane in expired gases. Exerpta/International Congress Series 1976; 387: 214-5.
2. Mono M, Fujii K, Satoh N, Imai M, Kawakami U, Mizuno T, Kawai Y, Ogasawara Y, Tamura T, Negishi A, Kumagi Y, Kawai T. Reaction of sevoflurane and its degradation products with soda lime. Toxicity of the by-products. Anesthesiology 1992; 77:1155-67.
3. Morita S, Latta W, Hambro K, Snider M T. Accumulation of methane, acetone and nitrogen in the inspired gas during closed circuit anesthesia. Anesthesia and Analgesia 1985; 64: 343-7.
4. Rolly G, Versichelen L F, Mortier E. Methane accumulation during closed-circuit anesthesia. Anesthesia and Analgesia 9194; 79: 545-7.
5. Lentz R. Carbon monoxide poisoning during anesthesia poses puzzles. Anesthesia Safety Foundation Newsletter 1994; 9: 13-14.
6. Moon R, Meyer A, Scott D, Fox E, Millington D, Norwood D. Intraoperative carbon monoxide toxicity. Anesthesiology; 73: A1049.
7. Moon R, Ingram C, Brunner E, Meyer A. Spontaneous generation of carbon monoxide within anesthetic circuits. Anesthesiology 1991; 75: A873.
8. Frink E J, Malan T P, Morgan S E, Brown E A, Malcomson M, Brown B R. Quantification of the degradation products of sevoflurane in two absorbents during low-flow anesthesia in surgical patients. Anesthesiology 1992: 77: 1064-9.
9. Bito H, Ikeda K. Closed-circuit anesthesia with sevoflurane in humans. Effects on renal and hepatic function and concentrations of breakdown products with soda lime in the circuit. Anesthesiology 1994: 80: 71-6.
10. Gonsowski C T, Laster M J, Eger E I, Ferrell L D, Kerschmann R L. Toxicity of compound A in rats. Effect of a 3-hour administration. Anesthesiology 1994: 80:556-65.
11. Gonsowski C T, Laster M J, Ferrell L D, Kerschmann R L. Toxicity of compound A in rats. Effect of increasing duration of administration. Anesthesiology 1994; 80: 566-73.
12. Carbon monoxide production from desflurane, enflurane, halothane, isoflurane, and sevoflurane with dry soda lime. Wissing H et al. *Anesthesiology* 2001 *November;* 95(5): 1205-12.

While an embodiment of the invention has been described in detail, that has been done for the purpose of illustration, not limitation.

The invention claimed is:

1. A system for removal of carbon dioxide and carbon monoxide from patient expired gas during anesthesia comprising:
   a) a molecular sieve bed having an input and an output and containing material which mechanically preferentially sequesters carbon dioxide and carbon monoxide within the structure of the sieve while not causing degradation of anesthetic gas;
   b) means for delivering gas expired from a patient undergoing anesthesia to the input of the molecular sieve bed;
   c) means for delivering processed gas from the output of the molecular sieve bed to an anesthesia machine; and
   d) means operatively connected to the input of the molecular sieve bed for providing a heated air purge to the bed during regeneration of the bed and at a temperature sufficient to pasteurize the bed.

2. The system according to claim 1, wherein the means for delivering gas to the input of the molecular sieve bed includes a drier for removing water vapor from the gas.

3. The system according to claim 1, wherein the means for delivering gas to the input of the molecular sieve bed includes a filter for removing particulate matter from the gas.

4. The system according to claim 1, further including means for operatively connecting a source of vacuum to the output of the molecular sieve bed for regenerating the bed.

5. The system according to claim 1, wherein the material contained in the molecular sieve bed is non-degrading to halogenated ether anesthetics.

6. The system according to claim 1, further including:
   a) one or more additional molecular sieve beds each having an input and an output and each containing material which mechanically preferentially sequesters carbon dioxide and carbon monoxide within the structure of the sieve while not causing degradation of anesthetic gas;
   b) means for delivering gas expired from a patient undergoing anesthesia to the inputs of the additional molecular sieve beds;
   c) means for delivering processed gas from the outputs of the molecular sieve beds to an anesthesia machine; and
   d) a control operatively connected to the means for delivering gas to the inputs of the beds and operatively connected to the means for delivering processed gas from the outputs of the beds for controlling cyclic operation of the beds.

7. The system according to claim 6, wherein the means for delivering gas to the inputs of the molecular sieve beds includes a drier for removing water vapor from the gas.

8. The system according to claim 6, wherein the means for delivering gas to the input of the molecular sieve beds includes a filter for removing particulate matter from the gas.

9. The system according to claim 6, further including means operatively connected to the control for selectively connecting a source of vacuum to the outputs of the molecular sieve beds for regenerating the beds.

10. The system according to claim 6, wherein the material contained in the molecular sieve beds is non-degrading to halogenated ether anesthetics.

11. A method for removal of carbon dioxide and carbon monoxide from patient expired gas during anesthesia comprising:
    a) providing a molecular sieve bed having an input and an output and containing material which mechanically preferentially sequesters carbon dioxide and carbon monoxide within the structure of the sieve while not causing degradation of anesthetic gas;
    b) delivering gas expired from a patient undergoing anesthesia to the input of the molecular sieve bed;
    c) delivering processed gas from the output of the molecular sieve bed to an anesthesia machine; and
    d) regenerating the molecular sieve bed by providing a heated air purge to the bed at a temperature sufficient to pasteurize the bed.

12. The method according to claim 11, wherein delivering gas to the input of the molecular sieve bed includes drying the gas to remove water vapor from the gas.

13. The method according to claim 11, wherein delivering gas to the input of the molecular sieve bed includes filtering the gas to remove particulate matter from the gas.

14. The method according to claim 11, further including connecting a source of vacuum to the output of the molecular sieve bed for regenerating the bed.

15. The method according to claim 11, wherein the material contained in the molecular sieve bed is non-degrading to halogenated ether anesthetics.

16. The method according to claim 11, further including:
    a) providing one or more additional molecular sieve beds each having an input and an output and each containing material which mechanically preferentially sequesters carbon dioxide and carbon monoxide within the structure of the sieve while not causing degradation of anesthetic gas;
    b) delivering gas expired from a patient undergoing anesthesia to the inputs of the additional molecular sieve beds;
    c) delivering processed gas from the outputs of the molecular sieve beds to an anesthesia machine; and
    d) controlling cyclic operation of the beds.

17. The method according to claim 16, wherein delivering gas to the inputs of the molecular sieve beds includes drying the gas to remove water vapor from the gas.

18. The method according to claim 16, wherein delivering gas to the inputs of the molecular sieve beds includes filtering the gas to remove particulate matter from the gas.

19. The method according to claim 16, further including selectively connecting a source of vacuum to the outputs of the molecular sieve beds for regenerating the beds.

20. The method according to claim 16, wherein the material contained in the molecular sieve beds is non-degrading to halogenated ether anesthetics.

21. A system for removal of carbon dioxide and carbon monoxide from patient expired gas during anesthesia comprising:
- a) a plurality of molecular sieve beds each having an input and an output and each containing material which mechanically preferentially sequesters carbon dioxide and carbon monoxide within the structure of the sieve while not causing degradation of anesthesia gas;
- b) means for delivering gas expired from a patient undergoing anesthesia individually to the inputs of the molecular sieve beds;
- c) means for delivering processed gas individually from the outputs of the molecular sieve beds to an anesthesia machine;
- d) a control operatively connected to the means for delivering gas individually to the inputs of the beds and operatively connected to the means for delivering processed gas individually from the outputs of the beds for controlling cyclic operation of the beds; and
- e) means operatively connected to the control and to the inputs of the molecular sieve beds for providing a heated air purge to the beds during regeneration of the beds and at a temperature sufficient to pasteurize the beds.

22. The system according to claim 21, further including means operatively connected to the control for selectively connecting a source of vacuum to the outputs of the molecular sieve beds for regenerating the beds.

23. A method for removal of carbon dioxide and carbon monoxide from patient expired gas during anesthesia comprising:
- a) providing a plurality of molecular sieve beds each having an input and an output and each containing material which mechanically preferentially sequesters carbon dioxide and carbon monoxide within the structure of the sieve while not causing degradation of anesthetic gas;
- b) delivering gas expired from a patient undergoing anesthesia individually to the inputs of the molecular sieve beds;
- c) delivering processed gas individually from the outputs of the molecular sieve beds to an anesthesia machine;
- d) controlling the delivering of gas of the inputs of the beds and the delivery of gas from the outputs of the beds in a manner providing cyclic operation of the beds; and
- e) regenerating the beds by providing a heated air purge to the beds at a temperature sufficient to pasteurize the beds.

24. The method according to claim 23, further including selectively connecting a source of vacuum to the outputs of the molecular sieve beds for regenerating the beds.

* * * * *